(12) United States Patent
Kahre et al.

(10) Patent No.: US 6,432,419 B2
(45) Date of Patent: *Aug. 13, 2002

(54) USE OF FATS TO REPLACE SILICONE IN COSMETIC AND/OR PHARMACEUTICAL PREPARATIONS

(75) Inventors: Joerg Kahre, Monheim; Achim Ansmann, Erkrath; Bernd Fabry, Korschenbroich; Rolf Kawa, Monheim; Werner Seipel, Hilden, all of (DE)

(73) Assignee: Cognis Deutschland GmbH, Dusseldorf (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/202,318

(22) PCT Filed: Jun. 3, 1997

(86) PCT No.: PCT/EP97/02866
§ 371 (c)(1),
(2), (4) Date: Feb. 4, 1999

(87) PCT Pub. No.: WO97/47281
PCT Pub. Date: Dec. 18, 1997

(30) Foreign Application Priority Data

Jun. 12, 1996 (DE) .......... 196 23 383

(51) Int. Cl.$^7$ .................. A61K 7/00
(52) U.S. Cl. .......... 424/401; 424/78.08; 514/785; 514/786; 252/174.23; 252/352; 252/358
(58) Field of Search .......... 424/401, 78.08; 514/785, 786; 252/174.23, 352, 358

(56) References Cited

U.S. PATENT DOCUMENTS

| | | | |
|---|---|---|---|
| 1,985,424 A | 12/1934 | Piggott | 260/124 |
| 2,016,962 A | 10/1935 | Flint et al. | 260/127 |
| 2,703,798 A | 3/1955 | Schwartz | 260/211 |
| 4,172,887 A | 10/1979 | Vanlerberghe et al. | 424/70 |
| 4,457,944 A * | 7/1984 | Conrad et al. | 424/358 |
| 4,919,923 A * | 4/1990 | Hoeffkes et al. | 424/70 |
| 5,194,250 A | 3/1993 | Fairhurst | 424/70 |
| 5,374,716 A | 12/1994 | Biermann et al. | 536/18.6 |
| 5,387,374 A | 2/1995 | Westfechtel et al. | 252/56 S |
| 5,409,628 A | 4/1995 | Heinz et al. | 252/174.17 |
| 5,449,475 A | 9/1995 | Cauwet et al. | 252/174.23 |
| 5,500,155 A * | 3/1996 | Weuthen et al. | 252/557 |
| 5,576,425 A | 11/1996 | Hill et al. | 536/18.6 |
| 5,686,087 A * | 11/1997 | Ansmann et al. | 424/401 |
| 5,795,978 A * | 8/1998 | Ansmann et al. | 536/120 |
| 5,817,254 A * | 10/1998 | Wadle et al. | 252/312 |
| 6,264,961 B1 * | 7/2001 | Ansmann et al. | 424/401 |

FOREIGN PATENT DOCUMENTS

| | | |
|---|---|---|
| CA | 1 000 203 | 11/1976 |
| CA | 2 145 474 | 10/1995 |
| DE | 11 65 574 | 4/1964 |
| DE | 20 24 051 | 12/1971 |
| DE | 2 134 451 | 12/1972 |
| DE | 31 33 078 | 3/1983 |
| DE | 36 36 256 | 4/1988 |
| DE | 40 40 154 | 6/1992 |
| DE | 41 19 890 | 12/1992 |
| DE | 41 29 986 | 3/1993 |
| DE | 43 41 794 | 1/1995 |
| DE | 44 11 557 | 10/1995 |
| DE | 44 20 880 | 12/1995 |
| EP | 0 014 509 | 8/1980 |
| EP | 0 301 298 | 2/1989 |
| EP | 0 357 186 | 3/1990 |
| EP | 0 531 650 | 3/1993 |
| EP | 0 603 078 | 6/1994 |
| EP | 0 674 898 | 10/1995 |
| FR | 2 252 840 | 6/1975 |
| GB | 962 919 | 7/1964 |
| GB | 1 333 475 | 10/1973 |
| WO | WO90/03977 | 4/1990 |
| WO | WO92/06984 | 4/1992 |
| WO | WO98/03155 | 1/1998 |

OTHER PUBLICATIONS

Kosmetik Und Aerosole in Seifen–Fette–Ole–Wachse, 100, (1974) pp. 173–177.
"Guerbet Alcohols" by A.J. O'Lennick in Soap/Cosmetics/Chemical Specialties, Apr. 1987, pp. 52–56.
Tenside Surfactants Detergents, 25, (1988) pp. 8–13.
"Kosmetische Faerbemittel" der Farbstoffkomission der Deutschen Forschungsgemeinschaft, Verlag Chemie, Weinheim, (1984), pp. 81–106.

* cited by examiner

Primary Examiner—Thurman K. Page
Assistant Examiner—Lakshmi Channevajjala
(74) Attorney, Agent, or Firm—John E. Drach; Henry E. Millson, Jr.

(57) ABSTRACT

A cosmetic or pharmaceutical composition free of silicone wherein the composition contains a fatty compound comprising an oil selected from the group consisting of
(a) dialkyl ethers,
(b) dialkyl cyclohexanes,
(c) Guerbet alcohols,
(d) polyol polyhydroxystearates, and
(e) hydroxycarboxylic acid esters.

12 Claims, No Drawings

USE OF FATS TO REPLACE SILICONE IN COSMETIC AND/OR PHARMACEUTICAL PREPARATIONS

This is a 371 of PCT/EP97/02866, filed Jun. 3, 1997.

BACKGROUND OF THE INVENTION

1. Field of the Invention

This invention relates to the use of selected fatty compounds as a substitute for silicones in the production of cosmetic and/or pharmaceutical preparations.

2. Discussion of Related Art

Silicones are used in skin and hair cosmetics as additives for influencing feel and luster. Unfortunately, the so-called build-up effect of silicones is a disadvantage. By this is meant that, when silicone-containing products are repeatedly applied to the skin or to the hair, a layer of polymers builds up and is difficult to remove simply by washing. In the case of hair in particular, this layer of polymers is undesirable and can interfere with other treatments, for example waving or dyeing. An overview of the use of silicones in cosmetics was published, for example, by K. Schnurrbusch in *Seifen-Fette-Öle-Wachse* 100, 173, (1974).

Accordingly, the problem addressed by the present invention was to provide silicone substitutes which would not build up in use, but which would still show at least comparable performance properties in regard to feel and luster.

2. Description of the Invention

The present invention relates to the use of fatty compounds as a silicone substitute in the production of cosmetic and/or pharmaceutical preparations which is distinguished by the fact that oils selected from the group consisting of
(a) dialkyl ethers,
(b) dialkyl cyclohexanes,
(c) Guerbet alcohols,
(d) Guerbet carbonates,
(e) ester oils,
(f) polyol polyhydroxystearates and/or
(g) hydroxycarboxylic acid esters
are used.

It has surprisingly been found that the sensorial evaluation of the selected oils in regard to feel and luster is at least as good as that of silicones without any unwanted build-up effect on skin and hair.

Dialkyl ethers

Dialkyl ethers which form component (a) correspond to formula (I):

$$R^1\text{—O—}R^2 \tag{I}$$

in which $R^1$ and $R^2$ independently of one another represent a linear or branched alkyl and/or alkenyl radical containing 6 to 22, preferably 8 to 18 and more preferably 12 to 18 carbon atoms. The ethers may have an asymmetrical structure, although they preferably have a symmetrical structure. Typical examples are di-n-octyl ether, di-i-octyl ether and di-n-stearyl ether.

Dialkyl cyclohexanes

Dialkyl cyclohexanes which form component (b) correspond to formula (II):

$$R^3\text{—[C]—}R^4 \tag{II}$$

in which $R^3$ and $R^4$ independently of one another represent a linear or branched alkyl and/or alkenyl group containing 6 to 22, preferably 8 to 18 and more preferably 12 to 18 carbon atoms and C is a cyclohexyl group. Typical examples are di-n-octyl cyclohexane, di-i-octyl cyclohexane and di-n-stearyl cyclohexane.

Guerbet alcohols

Guerbet alcohols which form component (c) are preferably obtained by base-catalyzed self-condensation of linear and/or branched alcohols containing 6 to 22 and preferably 8 to 18 carbon atoms. An overview of Guerbet alcohols was published by A. J. O'Lennick in *Soap Cosm. Chem. Spec.* (April) 52 (1987). Typical examples are condensation products of technical fatty alcohol cuts containing 8 to 10 or 16 to 18 carbon atoms.

Guerbet carbonates

Guerbet carbonates which form component (d) are normally obtained by complete or partial transesterification of dialkyl carbonates with linear and/or branched alcohols containing 6 to 22, preferably 8 to 18 and more preferably 12 to 18 carbon atoms [cf. U.S. 5,387,374 (Henkel)]. Typical examples are carbonates which are obtained by transesterification of dimethyl carbonate or diethyl carbonate with fatty alcohols containing 8 to 10 or 12 to 18 carbon atoms, preferably octanol or cetearyl alcohol.

Ester oils

Ester oils which form component (e) are long-chain esters liquid at room temperature which correspond to formula (III):

$$R^5CO\text{—}OR^6 \tag{III}$$

where $R^5CO$ is an aliphatic acyl group containing 6 to 22 carbon atoms and $R^6$ is an alkyl and/or alkenyl group containing 12 to 22 carbon atoms. Typical examples are esters of caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof with lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, eleaostearyl alcohol, arachyl alcohol, gadoleyl alcohol, behenyl alcohol, erucyl alcohol and brassidyl alcohol and technical mixtures thereof. Ester oils which contain at least 24 and preferably at least 30 carbon atoms and one double bond in the fatty acid and fatty alcohol component together are preferred. Typical examples are oleyl erucate, erucyl oleate, behenyl oleate and cetearyl oleate.

Polyol polyhydroxystearates

The polyol component of the polyol polyhydroxystearates which form component (f) may be derived from substances which contain at least 2, preferably 3 to 12 and more preferably 3 to 8 hydroxyl groups and 2 to 12 carbon atoms. Typical examples are glycerol and polyglycerol;

alkylene glycols, such as for example ethylene glycol, diethylene glycol, propylene glycol;

methylol compounds, such as in particular trimethylol ethane, trimethylol propane, trimethylol butane, pentaerythritol and dipentaerythritol;

alkyl oligoglucosides containing 1 to 22, preferably 1 to 8 and more preferably 1 to 4 carbon atoms in the alkyl group, such as for example methyl and butyl glucoside;

sugar alcohols containing 5 to 12 carbon atoms, such as for example sorbitol or mannitol, sugars containing 5 to 12 carbon atoms, such as for example glucose or sucrose;

amino sugars, such as for example glucamine.

Among the substances which form component (f), reaction products based on polyglycerol are particularly important by virtue of their excellent performance properties. It has proved to be of particular advantage to use selected polyglycerols with the following homolog distribution (the preferred ranges are shown in brackets):
glycerol: 5 to 35 (15 to 30)% by weight
diglycerols: 15 to 40 (20 to 32)% by weight
triglycerols: 10 to 35 (15 to 25)% by weight
tetraglycerols: 5 to 20 (8 to 15)% by weight
pentaglycerols: 2 to 10 (3 to 8)% by weight
oligoglycerols: to 100% by weight Hydrocarboxylic acid esters The last component (g) is selected from esters of hydroxycarboxylic acids containing 3 to 18 and preferably 3 to 12 carbon atoms with aliphatic alcohols containing 1 to 22, preferably 6 to 18 and more preferably 12 to 18 carbon atoms. Typical examples are esters of lactic acid, malic acid, tartaric acid, citric acid, ricinoleic acid and/or 12-hydroxystearic acid with methanol, ethanol, caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and technical mixtures thereof. It is preferred to use long-chain hydroxycarboxylic acids, such as ricinoleic acid and hydroxystearic acid, with short-chain alcohols, for example methanol or ethanol, or short-chain hydroxycarboxylic acids, such as lactic acid or citric acid, with long-chain fatty alcohols, such as for example cocofatty alcohol or cetearyl alcohol.

Surfactants

In one preferred embodiment of the invention, the sensorial properties of the fatty compounds can be further improved by mixing with nonionic surfactants, preferably of the alkyl and/or alkenyl oligoglycoside and/or fatty acid-N-alkyl glucamide type. In this embodiment, the fatty compounds and the nonionic surfactants may be used in a ratio by weight of 10:90 to 90:10, preferably in a ratio by weight of 25:75 to 75:25 and more preferably in a ratio by weight of 40:60 to 60:40.

Alkyl and/or alkenyl oligoglycosides

Alkyl and alkenyl oligoglycosides are known nonionic surfactants which correspond to formula (IV):

$$R^7O-[G]_p \quad\quad (IV)$$

where $R^7$ is an alkyl and/or alkenyl radical containing 4 to 22 carbon atoms, G is a sugar unit containing 5 or 6 carbon atoms and p is a number of 1 to 10. They may be obtained by the relevant methods of preparative organic chemistry. U.S. Pat. No. 5,374,716 and U.S. Pat. No. 5,576,425 are cited as representative of the extensive literature available on this subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides.

The index p in general formula (IV) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view.

The alkyl or alkenyl radical $R^7$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred. In addition, the alkyl or alkenyl radical $R^7$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ coconut oil fatty alcohol having a DP of 1 to 3 are preferred.

Fatty acid N-alkyl polyhydroxyalkylamides

Fatty acid N-alkyl polyhydroxyalkylamides are nonionic surfactants which correspond to formula (V):

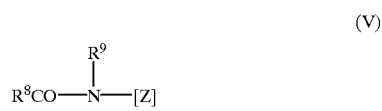

(V)

where $R^8CO$ is an aliphatic acyl radical containing 6 to 22 carbon atoms, $R^9$ is hydrogen, an alkyl or hydroxyalkyl radical containing 1 to 4 carbon atoms and [Z] is a linear or branched polyhydroxyalkyl radical containing 3 to 12 carbon atoms and 3 to 10 hydroxyl groups. The fatty acid N-alkyl polyhydroxyalkylamides are known compounds which may normally be obtained by reductive amination of a reducing sugar with ammonia, an alkylamine or an alkanolamine and subsequent acylation with a fatty acid, a fatty acid alkyl ester or a fatty acid chloride. Processes for their production are described in U.S. Pat. No. 1,985,424, in U.S. Pat. No. 2,016,962 and in U.S. Pat. No. 2,703,798 and in International patent application WO 92/06984. An overview of this subject by H. Kelkenberg can be found in Tens. Surf. Det. 25, 8 (1988).

The fatty acid N-alkyl polyhydroxyalkylamides are preferably derived from reducing sugars containing 5 or 6 carbon atoms, more particularly from glucose. Accordingly, the preferred fatty acid N-alkyl polyhydroxyalkylamides are fatty acid N-alkyl glucamides which correspond to formula (VI):

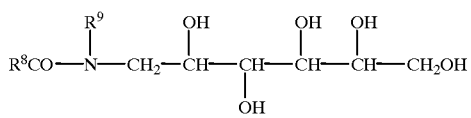

(VI)

Preferred fatty acid N-alkyl polyhydroxyalkylamides are glucamides corresponding to formula (VI) in which $R^9$ is hydrogen or an alkyl group and $R^8CO$ represents the acyl component of caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, arachic acid, gadoleic acid, behenic acid or erucic acid or technical mixtures thereof. Fatty acid N-alkyl glucamides (VI) obtained by reductive amination of glucose with methylamine and subsequent acylation with lauric acid or $C_{12/14}$ coconut oil fatty acid or a corresponding derivative are particularly preferred. In addition, the polyhydroxyalkylamides may also be derived from maltose and palatinose.

Commercial Applications

The silicone substitutes are suitable for the production of cosmetic and/or pharmaceutical preparations, preferably skin and hair treatment preparations, for example hair shampoos, hair lotions, foam baths, cremes, lotions or emollients. They may also contain emulsifiers, superfatting agents, stabilizers, waxes, consistency regulators, thickeners, cationic polymers, silicone compounds, biogenic agents, antidandruff agents, film formers, preservatives, hydrotropes, solubilizers, UV filters, dyes and perfumes as further auxiliaries and additives.

Suitable emulsifiers are, for example, nonionic surfactants from at least one of the following groups:

- adducts of 2 to 30 moles of ethylene oxide and/or 0 to 5 moles of propylene oxide with linear fatty alcohols containing 8 to 22 carbon atoms, with fatty acids containing 12 to 22 carbon atoms and with alkylphenols containing 8 to 15 carbon atoms in the alkyl group;
- $C_{12/18}$ fatty acid monoesters and diesters of adducts of 1 to 30 moles of ethylene oxide with glycerol;
- glycerol monoesters and diesters and sorbitan monoesters and diesters of saturated and unsaturated fatty acids containing 6 to 22 carbon atoms and ethylene oxide adducts thereof;
- adducts of 15 to 60 moles of ethylene oxide with castor oil and/or hydrogenated castor oil;
- partial esters based on linear, branched, unsaturated or saturated $C_{12/22}$ fatty acids, ricinoleic acid and 12-hydroxystearic acid and glycerol, polyglycerol, pentaerythritol, dipentaerythritol, sugar alcohols (for example sorbitol) and polyglucosides (for example cellulose);
- trialkyl phosphates;
- wool wax alcohols;
- polysiloxane/polyalkyl polyether copolymers and corresponding derivatives;
- mixed esters of pentaerythritol, fatty acids, citric acid and fatty alcohol according to DE-PS 11 65 574 and
- polyalkylene glycols.

The addition products of ethylene oxide and/or propylene oxide with fatty alcohols, fatty acids, alkylphenols, glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as refatting agents for cosmetic formulations from DE-PS 20 24 051.

In addition, zwitterionic surfactants may be used as emulsifiers. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Coco-amidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —$SO_3H$— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Besides ampholytic emulsifiers, quaternary emulsifiers may also be used, those of the esterquat type, especially methyl-quaternized difatty acid triethanolamine ester salts, being particularly preferred.

The superfatting agents used may be such substances as, for example, lanolin and lecithin and polyethoxylated or acylated lanolin and lecithin derivatives, polyol fatty acid esters, monoglycerides and fatty acid alkanolamides, the latter also serving as foam stabilizers. Suitable consistency regulators are, above all, fatty alcohols containing 12 to 22 and preferably 16 to 18 carbon atoms and, in addition, partial glycerides. These substances are preferably used in combination with alkyl oligoglucosides and/or fatty acid-N-methyl glucamides of the same chain length and/or polyglycerol poly-12-hydroxystearates. Suitable thickeners are, for example, polysaccharides, more particularly xanthan gum, guar guar, agar agar, alginates and tyloses, carboxymethyl cellulose and hydroxyethyl cellulose, relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols such as, for example, pentaerythritol or trimethylol propane, narrow-range fatty alcohol ethoxylates or alkyl oligoglucosides and electrolytes such as sodium chloride and ammonium chloride.

Suitable cationic polymers are, for example, cationic cellulose derivatives such as, for example, the quaternized hydroxyethyl cellulose available under the name of Polymer JR 400® from Amerchol, cationic starch, copolymers of diallyl ammonium salts and acrylamides, quaternized vinyl pyrrolidone/vinyl imidazole polymers such as, for example, Luviquate® (BASF), condensation products of polyglycols and amines, quaternized collagen polypeptides such as, for example, Lauryldimonium Hydroxypropyl Hydrolyzed Collagen (Lamequat®L Grünau), quaternized wheat polypeptides, polyethyleneimine, cationic silicone polymers such as, for example, Amidomethicone, copolymers of adipic acid and dimethyl aminohydroxypropyl diethylenetriamine (Cartaretine®, Sandoz), copolymers of acrylic acid with dimethyl diallyl ammonium chloride (Merquat® 550, Chemviron), polyaminopolyamides as described, for example, in FR-A 225840 and crosslinked water-soluble polymers thereof, cationic chitin derivatives such as, for example, quaternized chitosan, optionally in microcrystalline distribution, condensation products of dihaloalkyls such as, for example, dibromobutane with bis-dialkylamines such as, for example, bis-dimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol.

Suitable silicone compounds are, for example, dimethyl polysiloxanes, methyl phenyl polysiloxanes, cyclic silicones and amino-, fatty acid-, alcohol-, polyether-, epoxy-, fluorine- and/or alkyl-modified silicone compounds which may be both liquid and resin-like at room temperature. Typical examples of fats are glycerides while suitable waxes are inter alia beeswax, carnauba wax, candelilla wax, montan wax, paraffin wax or microwaxes, optionally in combination with hydrophilic waxes, for example cetostearyl alcohol, or partial glycerides. The pearlescent waxes used may be, in particular, mono- and difatty acid esters of polyalkylene glycols, partial glycerides or esters of fatty alcohols with polybasic carboxylic acids or hydroxycarboxylic acids. Suitable stabilizers are metal salts of fatty acids such as, for example, magnesium, aluminium and/or zinc stearate. Biogenic agents in the context of the invention are, for example, tocopherol, tocopherol acetate, tocopherol palmitate, ascorbic acid, retinol, bisabolol, allantoin, phytantriol, panthenol, AHA acids, plant extracts and vitamin complexes. Suitable antidandruff agents are climbazol, octopirox and zinc pyrethion. Typical film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds. In addition, hydrotropes such as, for example, ethanol, isopropyl alcohol or polyols may be used to improve flow behavior. Suitable preservatives are, for example, phenoxyethanol, formaldehyde solution, parabens, pentanediol or sorbic acid. Suitable dyes are any of the substances suitable and approved for cosmetic purposes as listed, for example, in the publication "*Kosmetische Färbemittel*" of the *Farbstoffkommission der Deutschen Forschungsgemeinschaft, Verlag Chemie, Weinheim,* 1984, pages 81 to 106, These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular formulation. The formulations may be prepared by standard cold or hot processes and are preferably produced by the phase inversion temperature method.

EXAMPLES

Various hair shampoos containing the silicone substitutes according to the invention (formulations F1 to F7) or silicone (comparison formulation F8) were evaluated for feel and luster on a scale of 1 (=pleasant soft feel, brilliant luster) to 5 (=hard, dull) by a panel of 20 volunteers in the known half-head test. For qualitatively determining the build-up of the oils on the hair, hair tresses were alternately treated with the test formulations and dried 10 times and then reduced to ashes. A heavy build up of oils is indicated by the symbol (+) in the Table whereas the symbol (−) indicates the absence or substantial absence of oils. The results represent mean values.

TABLE 1

Hair shampoos: feel and luster (quantities in % by weight)

| Components | F1 | F2 | F3 | F4 | F5 | F6 | F7 | F8 |
|---|---|---|---|---|---|---|---|---|
| Sodium Laureth Sulfate | | | | 15 | | | | |
| Cocoamidopropyl Betaine | | | | 3 | | | | |
| PEG Distearate | | | | 3 | | | | |
| Dicaprylyl ether | 1 | — | — | — | — | — | — | — |
| Dicaprylyl cyclohexane | — | 1 | — | — | — | — | — | — |
| Octyldodecanol | — | — | 1 | — | — | — | — | — |
| Octyldodecyl carbonate | — | — | — | 1 | — | — | — | — |
| Oleyl erucate | — | — | — | — | 1 | — | — | — |
| PEG hydroxystearate | — | — | — | — | — | 1 | — | — |
| Oleyl lactylate | — | — | — | — | — | — | 1 | — |
| Dimethicone | — | — | — | — | — | — | — | 1 |
| NaCl | | | | 0.5 | | | | |
| Water | | | | to 100 | | | | |
| Evaluation (half-head test) | | | | | | | | |
| - Feel | 2 | 2.5 | 2.5 | 1.5 | 2 | 1.5 | 2 | 2.5 |
| - Luster | 1 | 1 | 1.5 | 2.5 | 2 | 2 | 2 | 3 |
| - Build-up | — | — | — | — | — | — | — | + |

Hair aftertreatment formulations F9 to F15 and comparison product F16 were tested in the same way. The results are set out in Table 2.

TABLE 2

Hair aftertreatment formulations: feel and luster (quantities in % by weight)

| Components | F9 | F10 | F11 | F12 | F13 | F14 | F15 | F16 |
|---|---|---|---|---|---|---|---|---|
| Cetearylalcohol | | | | 3 | | | | |
| Cetrimmonium chloride | | | | 4 | | | | |
| Glyceryl Stearate | | | | 3 | | | | |
| Dicaprylyl ether | 1 | — | — | — | — | — | — | — |
| Dicaprylyl cyclohexane | — | 1 | — | — | — | — | — | — |
| Octyldodecanol | — | — | 1 | — | — | — | — | — |
| Octyldodecyl carbonate | — | — | — | 1 | — | — | — | — |
| Oleyl erucate | — | — | — | — | 1 | — | — | — |
| PEG hydroxystearate | — | — | — | — | — | 1 | — | — |
| Oleyl lactylate | — | — | — | — | — | — | 1 | — |
| Dimethicone | — | — | — | — | — | — | — | 1 |
| NaCl | | | | 0.5 | | | | |
| Water | | | | to 100 | | | | |

TABLE 2-continued

Hair aftertreatment formulations: feel and luster (quantities in % by weight)

| Components | F9 | F10 | F11 | F12 | F13 | F14 | F15 | F16 |
|---|---|---|---|---|---|---|---|---|
| Evaluation (half-head test) | | | | | | | | |
| - Feel | 2.5 | 2 | 1.5 | 1.5 | 2.5 | 1 | 2.5 | 3 |
| - Luster | 1 | 1.5 | 1 | 2 | 2.5 | 2 | 2.5 | 3.5 |
| - Build-up | — | — | — | — | — | — | — | + |

The panel tests show that the use of the fatty compounds according to the invention leads to formulations which, when applied to the hair, are judged to be better than the comparison formulations containing silicones and which, at the same time, have the advantage of no build-up effect.

What is claimed is:

1. In a cosmetic or pharmaceutical composition selected from the group consisting of hair shampoos, hair lotions, cosmetic or pharmaceutical creams, cosmetic or pharmaceutical lotions, cosmetic or pharmaceutical emollient compositions, wherein said compositions contain at least one of the following auxiliaries and/or additives;

an emulsifier,
a superfatting agent,
a stabilizer,
a wax,
a consistency regulator,
a thickener,
a cationic polymer,
a silicone compound,
a biogenic agent,
an antidandruff agent,
a film former,
a preservative,
a hydrotrope,
a solubilizer,
a UV filter,
a dye,
a perfume, the improvement wherein the composition contains:
I) a nonionic surfactant selected from the group consisting of alkyl or alkenyl oligoglycosides and fatty acid-N-alkyl polyhydroxyalkylamides; and
II) a fatty compound wherein said fatty compound consists of an oil selected from the group consisting of
a) polyol polyhydroxystearates; and
b) hydroxycarboxylic acid esters wherein said fatty compound and said nonionic surfactant are present in a ratio by weight of 10:90 to 90:10; and
III) wherein the total quantity of auxiliaries and/or additives in the composition is from 1 to 50% by weight, based on the weight of the composition.

2. A composition as in claim 1 wherein component II, is a polyol polyhydroxystearate.

3. A composition as in claim 1 wherein component II, is a hydroxycarboxylic acid ester comprising esters of hydroxycarboxylic acids containing 3 to 18 carbon atoms with aliphatic alcohols containing 1 to 22 carbon atoms.

4. In a cosmetic or pharmaceutical composition selected from the group consisting of hair shampoos, hair lotions, cosmetic or pharmaceutical creams, cosmetic or pharmaceutical lotions, cosmetic or pharmaceutical emollient compositions, wherein said compositions contain at least one of the following auxiliaries and/or additives.

an emulsifier,
a superfatting agent,
a stabilizer,
a wax,
a consistency regulator,
a thickener,
a cationic polymer,
a biogenic agent,
an antidandruff agent,
a film former,
a preservative,
a hydrotrope,
a solubilizer,
a UV filter,
a dye,
a perfume, the improvement comprising:
I) the composition contains a nonionic surfactant selected from the group consisting of alkyl or alkenyl oligoglycosides and fatty acid-N-alkyl polyhydroxyalkylamides;
II) the composition is free from silicone components;
III) the composition contains a fatty compound consisting of an oil selected from the group consisting of
a) polyol polyhydroxystearates; and
b) hydroxycarboxylic acid esters;
wherein said fatty compound and said nonionic surfactant are present in a ratio by weight of 10:90 to 90:10; and
IV) the total quantity of auxiliaries and/or additives is from 1 to 50% by weight, based on the weight of the composition.

5. A composition as in claim 4 wherein component (III) is a polyol polyhydroxystearate.

6. A composition as in claim 4 wherein component (III) is a hydroxycarboxylic acid ester comprising esters of hydroxycarboxylic acids containing 3 to 18 carbon atoms with aliphatic alcohols containing 1 to 22 carbon atoms.

7. The composition of claim 1 wherein said ratio by weight is from 25:75 to 75:25.

8. The composition of claim 1 wherein said ratio by weight is from 40:60 to 60:40.

9. The composition of claim 4 wherein said ratio by weight is from 25:75 to 75:25.

10. The composition of claim 4 wherein said ratio by weight is from 40:60 to 60:40.

11. The composition of claim 1 wherein the total quantity of auxiliaries and/or additives is from 5 to 40% by weight.

12. The composition of claim 4 wherein the total quantity of auxiliaries and/or additives is from 5 to 40% by weight.

* * * * *